United States Patent
Scheinberg et al.

(10) Patent No.: US 7,087,806 B2
(45) Date of Patent: Aug. 8, 2006

(54) FRICTION REDUCING DEVICES

(75) Inventors: Samuel Scheinberg, Otis, OR (US); Adrian A. Polliack, Lake Oswego, OR (US); Joseph Tuholsky, Burnsville, MN (US)

(73) Assignee: Advanced Wound Systems, LLC, Newport, OR (US)

( * ) Notice: Subject to any disclaimer, the term of this patent is extended or adjusted under 35 U.S.C. 154(b) by 0 days.

(21) Appl. No.: 10/672,731

(22) Filed: Sep. 25, 2003

(65) Prior Publication Data

US 2005/0033212 A1 Feb. 10, 2005

Related U.S. Application Data

(63) Continuation-in-part of application No. 10/637,429, filed on Aug. 8, 2003, now abandoned.

(51) Int. Cl.
*A61F 5/00* (2006.01)

(52) U.S. Cl. .......................... 602/41; 128/889
(58) Field of Classification Search ............ 602/41–59; 128/888–889; 2/69; D24/189; 424/443–449; 604/304–308

See application file for complete search history.

(56) References Cited

U.S. PATENT DOCUMENTS

| | | | |
|---|---|---|---|
| 1,913,928 A | 6/1933 | Kaufman | |
| 2,098,312 A | 11/1937 | Scholl | |
| 2,261,041 A | 10/1941 | Tennant | |
| 2,669,989 A | 2/1954 | Shoucair | |
| 2,712,311 A | 7/1955 | Scholl | |
| 2,817,335 A | 12/1957 | Thompson | |
| 2,918,062 A | 12/1959 | Scholl | |
| 3,062,208 A | 11/1962 | Scholl | |
| 3,260,261 A | 7/1966 | Gallovich | |
| 3,548,420 A | 12/1970 | Spence | |
| 3,821,954 A | 7/1974 | Grubel | |
| 3,968,530 A | 7/1976 | Dyson | |
| 4,572,174 A | 2/1986 | Eilender et al. | |
| 4,600,001 A | 7/1986 | Gilman | |
| 4,729,369 A | 3/1988 | Cook | |
| 4,959,059 A | 9/1990 | Eilender et al. | |
| 5,012,801 A | 5/1991 | Feret | |
| RE33,727 E | 10/1991 | Sims | |
| 5,170,781 A * | 12/1992 | Loomis | 128/118.1 |
| 5,188,124 A | 2/1993 | Feret | |
| 5,462,519 A | 10/1995 | Carver | |
| 5,512,041 A * | 4/1996 | Bogart | 602/58 |
| 5,590,420 A * | 1/1997 | Gunn | 2/69 |
| 5,665,060 A | 9/1997 | Fabricant | |
| 5,899,207 A | 5/1999 | Scheinberg | |
| 6,067,987 A | 5/2000 | Scheinberg | |

(Continued)

FOREIGN PATENT DOCUMENTS

EP 0051935 A2 5/1982

*Primary Examiner*—Kim M. Lewis
(74) *Attorney, Agent, or Firm*—Chernoff, Vilhauer, McClung & Stenzel, LLP (57) ABSTRACT

A self-adhesive bandage for prevention and treatment of skin breakdown by relief of friction and shear forces. The bandage includes a pair of thin film membranes, one of which is a portion of a dome and is free to move a limited distance with respect to the other. The dome is located on a skin contact layer that can be adhered to one's skin. A method of making such a bandage includes forming a dome in a flexible film and adhesively attaching a skirt surrounding the dome to a skin contact layer. Similar friction reducing devices may be incorporated in shoes, other clothing, or sports equipment.

44 Claims, 8 Drawing Sheets

U.S. PATENT DOCUMENTS

| | | |
|---|---|---|
| 6,169,224 B1 | 1/2001 | Heinecke et al. |
| 6,222,090 B1 * | 4/2001 | Weston ........................ 602/41 |
| D446,307 S * | 8/2001 | Bassett ...................... D24/189 |
| 6,274,787 B1 * | 8/2001 | Downing ..................... 602/41 |
| 6,320,093 B1 * | 11/2001 | Augustine et al. ............ 602/41 |
| 6,362,387 B1 * | 3/2002 | Carlson et al. ................ 602/41 |
| 6,570,050 B1 * | 5/2003 | Augustine et al. ............ 602/41 |
| D483,491 S * | 12/2003 | Grady et al. ................ D24/189 |
| D493,000 S * | 7/2004 | Grady et al. ................ D24/189 |

* cited by examiner

FRICTION REDUCING DEVICES

CROSS REFERENCE TO RELATED APPLICATIONS

This application is a continuation-in-part of U.S. patent application Ser. No. 10/637,429, filed Aug. 8, 2003 now abandoned.

BACKGROUND OF THE INVENTION

The present invention relates to prevention and treatment of irritation, discomfort, pain and skin breakdown resulting from shear and friction forces, and pressure against an area of skin.

Friction and shear forces are two factors that play a significant role in causing breakdown of skin and the underlying tissues, which can lead to erythema (red spots), blisters and pressure ulcers. Friction and shear forces commonly occur at the skin-support interface, e.g. where the skin contacts another surface such as in malfitting footwear, bedding, wheelchairs, under casts and under the socket of a prosthesis (artificial limb). Skin breakdown can also occur following rubbing on skin areas contacted by undergarments, athletic equipment, and clothing, skin of hands operating industrial equipment and machinery, and in many other instances where repeated rubbing of skin occurs. The present invention relates to reducing the friction and shear forces contributing to these disabling and serious conditions.

Scheinberg U.S. Pat. Nos. 5,899,207 and 6,067,987 disclose a tissue-protective device including mutually overlying membranous layers arranged to be able to slip easily along each other at the interface between the skin and an adjacent surface, e.g. a shoe, another article of clothing or equipment pressing against or moving along the surface of skin, and internally between soft tissues in vivo, for protection from friction. The devices disclosed by Scheinberg, however, are not particularly well adapted for mass production.

What is desired, then, is a dressing or bandage which can readily be mass-produced in a form easily used by application to a person's skin or by incorporation in an article of clothing or other article that may cause friction, shearing, or pressure on the skin, either to prevent skin breakdown and reduce irritation, discomfort and pain, or to protect and enhance healing of an area of a person's skin which has already been damaged by rubbing and pressure. Preferably such an improved device should be thin, in order to avoid creating additional pressure to the skin and underlying tissues, while greatly reducing shear and friction forces encountered by the skin. Such a bandage should be flexible, so that it can be easily contoured to complex curvatures of anatomical sites such as the heel, ankles and elbows. It should also be able to stretch and move with the skin during activity. A method for economically making such a dressing, bandage, or other device is also needed.

SUMMARY OF THE INVENTION

The present invention provides a bandage that overcomes some of the shortcomings of previously available devices for protecting a person's skin from injury or irritation, and also provides a method of manufacturing such an article.

In one embodiment of the invention, a protective bandage includes a skin contact layer of a flexible film. A hollow dome of flexible film is attached to the skin contact layer and is free to move along the skin contact layer through a distance related to the height of the dome, while the side of the skin contact layer opposite the dome can be attached to a person's skin by an adhesive.

In one embodiment, the dome includes a dome top layer of flexible film defining the shape of the dome, and a substantially flat dome base layer of similar film material. The dome top layer is attached to the dome base layer, so that the dome top layer can slide along the surface of the dome base layer and the dome base layer is attached directly to the skin contact layer.

As a feature of one embodiment, the skin contact layer is of a flexible film material which is more elastic than the film material of the dome, and the skin contact layer extends beyond the dome to attach the dome securely to a person's skin, yet conform to and stretch and relax with the skin to which it is attached as the person moves.

In one embodiment of the bandage, the skin contact layer is perforated, to enhance moisture and vapor transfer from the person's skin, and add to flexibility of the skin contact layer. Perforation may be omitted near a boundary between the material defining the dome and the portions of the skin contact layer that extend beyond the dome material.

In one embodiment of the invention, the friction reducing structure may be incorporated in an article of clothing or sports equipment against which a person's skin may be in frequent contact.

A method of making a bandage according to the invention includes forming a flexible dome including a side wall in a flexible film, leaving the dome surrounded by a generally planar skirt, and thereafter attaching the skirt adhesively to a skin contact layer of flexible film.

A method of manufacturing a bandage according to the present invention includes defining openings corresponding with the size of domes for the bandages in a sheet of transfer adhesive material, applying the transfer adhesive to a web of flexible film material, thereafter forming the film material within the openings to define domes, and thereafter using the adhesive layer to attach each dome to a layer of film material.

The foregoing and other objectives, features and advantages of the present invention will be more readily understood upon consideration of the following detailed description of the invention taken in conjunction with the accompanying drawings.

DETAILED DESCRIPTION OF THE PREFERRED EMBODIMENTS

Referring to FIGS. 1–4 of the drawings which form a part of the disclosure herein, an elliptical bandage 14 which is one preferred embodiment of the present invention includes a skin contact layer 16 of flexible film material to which a layer 18 of an adhesive material is adhered. The layer 18 of adhesive material is protected by an easily removable liner 20 divided into two separate halves by a cut 22 extending across the liner 20 to allow the halves of the liner 20 to be removed separately during application of the bandage 14 to a person's skin. Alternatively, one part of the liner 20 can overlap the other along the location of the cut 22, with the overlying portion including a folded-back margin flap 23 shown in broken line, to facilitate removal of the liner 20 from the skin contact layer 20 to apply the bandage. As one preferred size, the bandage 14 may have a length 24 of 66.67 mm (2.625 in.) and a width 26 of 38.1 mm (1.5 in.).

A dome 28 is centrally located on and adhesively attached to the skin contact layer 16. The dome 28 includes a top portion 30 and a circumferential side wall portion 32 interconnecting the top portion with the skin contact layer 16 and with intermediate portions of the bandage 14, as will be described in more detail presently. The dome 28 is of a thin, strong, flexible, film material, and its top portion 30 is free to move parallel with the skin contact layer 16 in any direction from a neutral position, as limited principally by the height 33 of the side wall portion 32 of the dome. The dome may have a diameter 29 of 25.15 mm (0.990 in.), and the top portion 30 may have a diameter 31 of 22.86 mm (0.0900 in.), for example, and the dome 28 may have a height 33 of 4.76 mm (0.1875 in.).

As shown in FIGS. 2–5, in the preferred embodiment of the bandage 14, the dome 28 includes a dome top layer 36 and a dome base layer 38. The dome base layer 38 is fastened to a first, or upper, side of the skin contact layer 16, for example being adhesively attached by a layer of adhesive material 40 that is coextensive with the dome base layer 38.

As used herein, the term adhesively attached should be understood to include the use of various mechanisms such as thermal fusion, ultrasonic fusion, and chemical fusion to interconnect layers of the bandage 14, as well as the use of layers of adhesive materials such as the particular pressure sensitive adhesives described herein in detail.

The dome top layer 36 includes the top portion 30, the side wall portion 32, and a skirt portion 42 that is generally flat and which surrounds and extends radially outward in all directions from the base of the side wall portion 32. The skirt portion 42 is adhesively attached to the dome base layer 38 and the skin contact layer 16, as by a layer 44 of adhesive material. The layer 44 of adhesive material is coextensive with the skirt portion 42 but does not extend onto the side wall portion 32 or the top portion 30 of the dome 28.

The skin contact layer 16 is larger than either the dome base layer 38 or the dome top layer 36 and preferably has an elliptical or other elongated oval shape, extending away from the dome 28 in both of a pair of opposite directions to opposite ends 48 and 50. Other shapes could also be useful for use of the bandage 14 in a particular place.

The dome base layer 38 has a pair of opposite and parallel straight margins 52 extending transversely across the skin contact layer 16, while arcuate opposite ends 54 of the dome base layer 38 coincide with portions of the side margins 56 of the skin contact layer 16. The skirt portion 42 of the dome top layer 36 similarly has a pair of parallel straight margins 58 and a pair of arcuate opposite ends 60 which also coincide with portions of the side margins 56 of the skin contact layer 16.

The straight margins 58 of the dome top layer 36 are separated from each other by a distance 72 that is somewhat greater than the distance 70 between the parallel straight margins 52 of the dome base layer 38, so that each straight margin 58 extends beyond the adjacent straight margin 52 toward a respective nearer one of the opposite ends 48 and 50 of the skin contact layer 16 on either end of the bandage 14. For example, the width 70 of the dome base layer 38 between its straight margins 52 is preferably 28.6 mm (1.125 in.), while the width 72 of the dome top layer 36 may be 31.75 mm (1.25 in.), so that a portion of the skirt portion 42 attached to the skin contact layer 16 overlaps the dome base layer 38 on each side by a width 74 of about 1.6 mm (0.0625 in) beyond the straight margin 52. The adhesive layer 44 thus attaches the dome top layer 36 both to the dome base layer 38, in an area surrounding the dome 28, and to the first or upper side of the skin contact layer 16, in narrow areas between the straight margins 52 and 58, between the dome 28 and each of the opposite ends 48 and 50 of the skin contact layer 16. This arrangement with the margins 58 of the skirt portion 42 overlapping beyond the margins 52 provides a smooth contour of the bandage 14 in the connection of the dome top layer 36 to the skin contact layer 16, and adds to security of the connection of the dome 28 to the skin contact layer 16.

Since the adhesive layer 44 is present only on the skirt portion 42 of the dome top layer 36, the top portion 30 of the dome is free from the opposing upper surface of the dome base layer 38. The top portion 30 thus can move parallel with and along the upper surface of the dome base layer 38 in any direction in which it is urged, to the extent that it is permitted to move by the height 33 of the side wall portion 32. The thin film material of the dome top layer 36 and dome base layer 38 is a flexible and strong membrane, and has a low enough coefficient of friction, when rubbing against surfaces of similar material, that there is significantly less friction between the top portion 30 of the dome and the dome base layer 38 than is likely between, for example, a person's skin and a sock pressed against the skin by the inside of a shoe.

Figure 1:
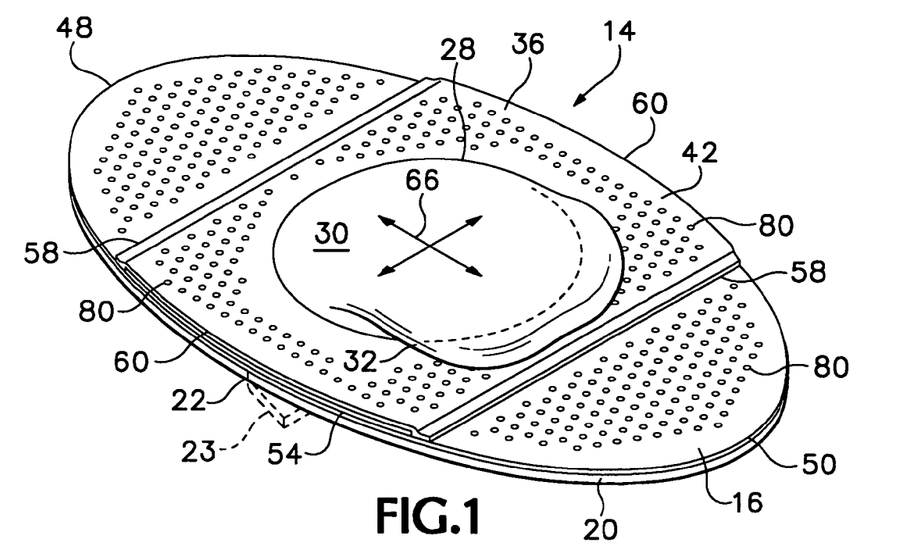
FIG. 1 is a perspective view of a bandage which is one preferred embodiment of the present invention.
Figure 2:
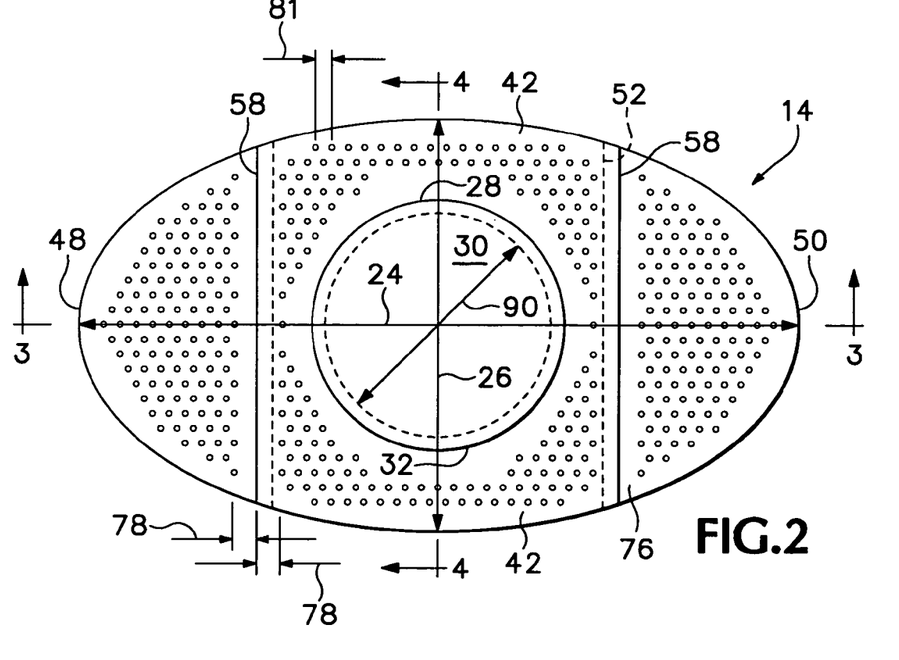
FIG. 2 is a top plan view of the bandage shown in FIG. 1.
Figure 3:
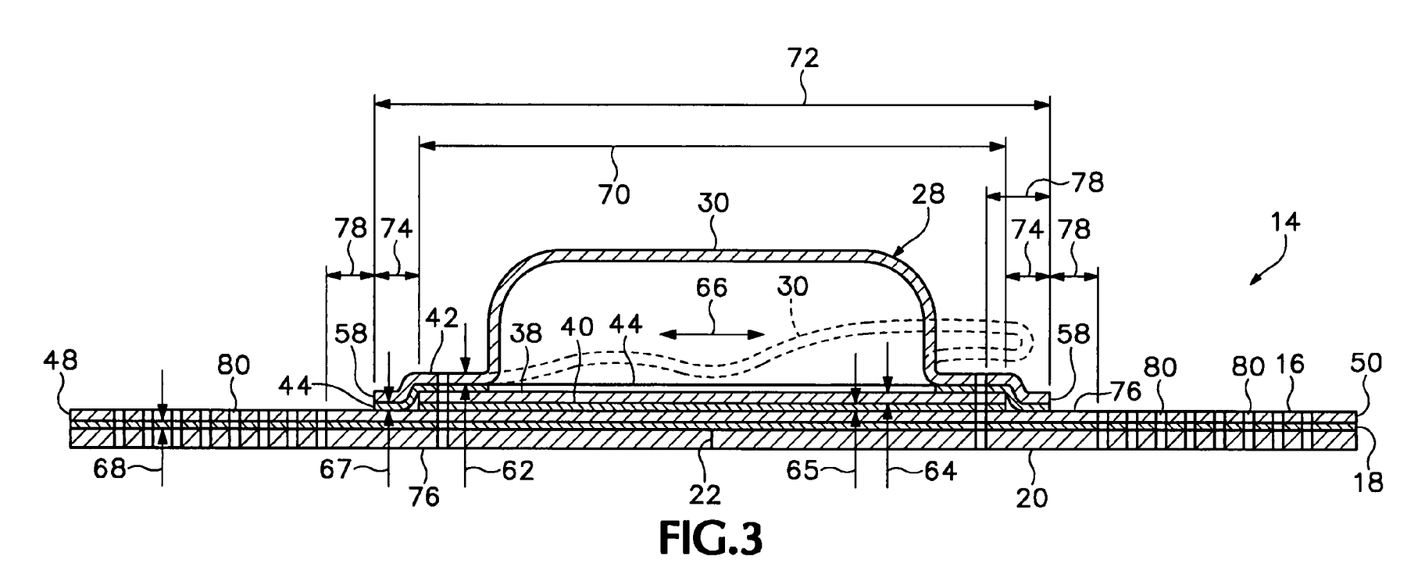
FIG. 3 is a section view taken on line 3—3 of FIG. 2 with thicknesses greatly exaggerated.
Figure 4:
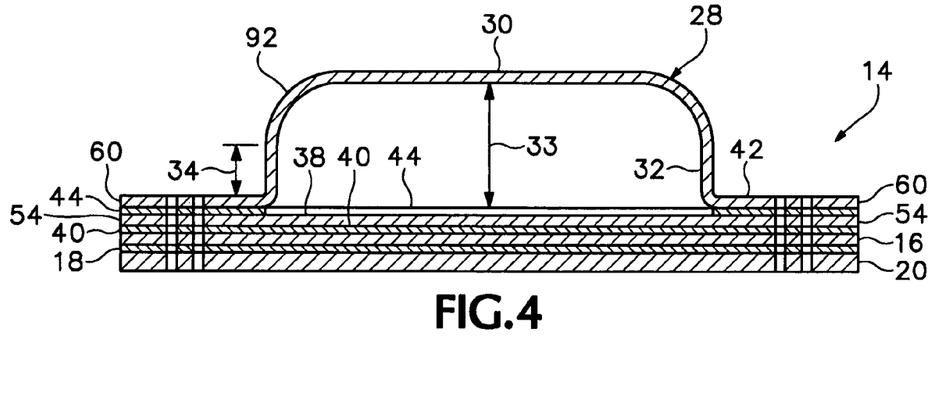
FIG. 4 is a section view taken on line 4—4 of FIG. 2 with thicknesses greatly exaggerated.
Figure 5:
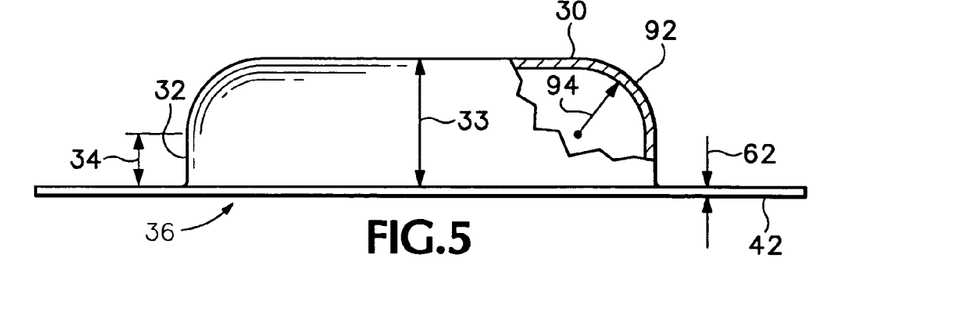
FIG. 5 is a partially cutaway sectional detail view of the dome top layer of the bandage, taken in the direction indicated by line 4—4 of FIG. 2.

The film of which the dome top layer 36 may also be somewhat pervious to gas, so that the dome 28 can inflate, deflate, or collapse, according to the design of a particular dome, and particular material used as the dome top layer 36. The top portion 30 can contact and move in any direction along the dome base layer 38 (or the skin contact layer 16, should there be no dome base layer 38), as indicated by the arrow 66. Thus, while the dome 28 is shown in a neutral position in FIGS. 2–5, it is shown in FIG. 1 in a collapsed condition and offset toward the end 50 of the base layer 16, as also indicated in broken line in FIG. 3.

In order to protect a portion of a person's skin exposed to pressure or rubbing without adding to potential irritation, the entire bandage 14 is flexible and preferably as thin as practical consistent with sufficient strength. Accordingly, the dome top layer 36 may be of polyethylene film having a thickness 62 of about 25 microns (1 mil), and the dome base layer 38 is preferably of similar film material also having a thickness 64 of about 25 microns (1 mil). In such a small thickness, the polyethylene is amply flexible yet strong enough to withstand the usual forces to be encountered. A suitable polyethylene film is available in such a thickness from Quality Extrusion of Mankato, Minn., as its QCE 5% EVA type A polyethylene film.

Preferably, the adhesive layers 40 and 44 respectively interconnecting the dome base layer 38 with the skin contact layer 16 and interconnecting the skirt portion 42 of the dome top layer 36 with the dome base layer 38 and the skin contact layer 16 have similar thicknesses 65 and 67 of about 25 microns (1 mil). One suitable transfer adhesive is a non-sensitizing medical grade, biocompatible transfer adhesive, available from Tyco Adhesives of Norwood, Mass., as its "TR 2295C Medical Grade Transfer Adhesive," in the form of a coiled transfer tape, a web of adhesive material carried on a backing or liner that is relatively easily removable after the adhesive is mated with the polyethylene film material of either the dome top layer 36 or the dome base layer 38.

A suitable material for the skin contact layer 16 is a polyurethane film having a thickness 68 of about 50 microns (2 mils). Such a polyurethane film is suitably strong and flexible and also is slightly more elastic than polyethylene, and thus is more able to conform to a person's skin as the skin stretches and relaxes during movement, than the polyethylene material preferred for the dome top layer 36 and base layer 38.

An acceptable polyurethane film for use as the skin contact layer 16 is available from Avery Dennison Medical, of Mentor, Ohio, in such a thickness, together with a non-sensitizing, pressure sensitive, acrylic copolymer adhesive coating on one face of the film and ready for use as the adhesive layer 18, and with a silicone coated kraft paper liner already adhered to the layer 18 of adhesive material. Such a laminated material is available from Avery Dennison Medical as its MED 5042 polyurethane film.

The bandage 14 in use thus has a thickness (excluding the liner 20) of not more than about 0.15 mm (6 mils), so as to avoid aggravating pressure on one's skin by added bulk, as inside a shoe, for example.

For still thinner bandages, one may use materials chosen to have a low coefficient of friction between the dome top layer 36 and the skin contact layer 16, or may include a small amount of suitable lubricant (not shown) between the dome top layer 36 and the skin contact layer 16. In this configuration, the dome base layer 38 might be omitted, although this may require a compromise with respect to either the ability of the dome 28 to move easily with respect to the skin contact layer 16, or to the ability of the skin contact layer 16 to conform to the user.

The bandage 14 is preferably perforated to aid in transmission of vapor and moisture from the skin to which the bandage 14 may be attached. Such perforation may also enhance the flexibility of the skin contact layer and its ability to stretch. Arrays of perforations 80 are preferably present within the opposite end portions 48 and 50 and within the skirt portion 42, but perforations may or may not be present in the dome 28 itself. Perforations 80 are preferably separated by only a small spacing 81, such as 1.27 mm (0.050 in.), and preferably in the range of 0.76–2.28 mm (0.030–0.090 in). An area 76 extending along each of the straight margins 58 of the dome top layer 36 is preferably free from perforations, in order to avoid interference with the stability of adhesive attachment of the dome 28 to the skin contact layer 16. For example, an area 76 extending for a distance 78 of about 1.6 mm (0.0625 in) on either side of each of the straight margins 58 is left free from perforations 80 in the bandage 14 described herein above.

Figure 6:
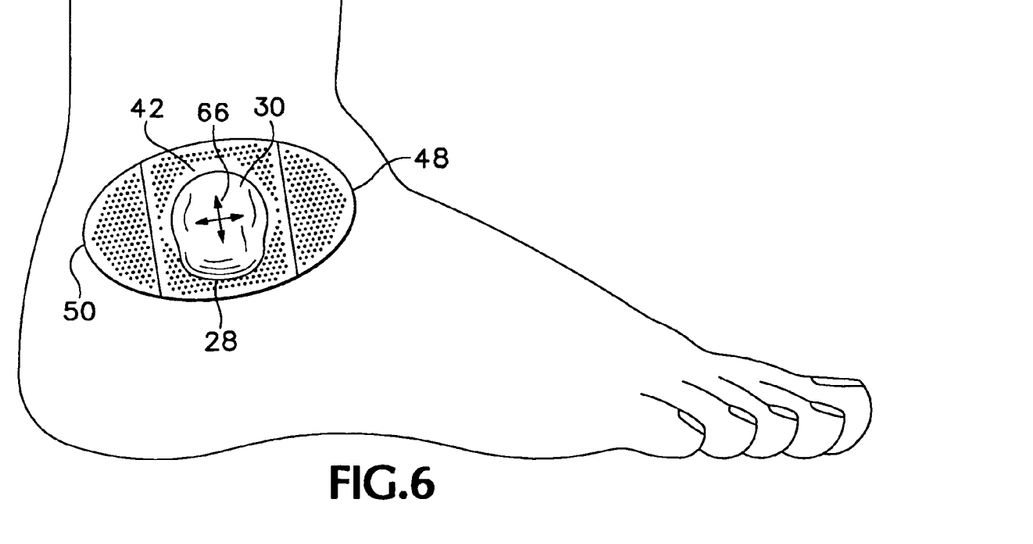
FIG. 6 is a view showing the bandage shown in FIG. 1 in place on a person's ankle.

The bandage 14 can be applied to a person's skin with the dome 28 aligned with a portion of the skin which otherwise might be rubbed by an article interfacing with the person's skin, such as a wheelchair, bedclothing, shoes, athletic equipment, etc. As shown in FIG. 6, the dome 28 is aligned with the prominence on the outside of a person's ankle, and the top portion 30 of the dome 28 is free to move relative to the skirt 42 and the underlying dome base layer 38, while the skin contact layer 16 is securely attached to the person's skin by its adhesive layer 18. The flexibility and elasticity of the skin contact layer 16 permit it to conform easily to the person's ankle, and to stretch and retract itself as the person undergoes activity. The top portion 30 of the dome 28 is free to move in any direction, as indicated by the arrow 66, within the limitations imposed by the height of the dome 28, as previously explained.

Figure 7:
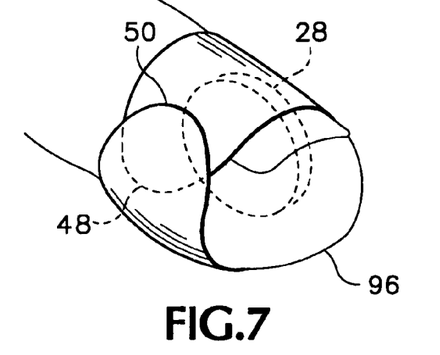
FIG. 7 is a perspective view of the bandage shown in FIG. 1, in place on a person's toe.

The length 24 of the bandage 14, or another bandage of like construction but different size, is intended to permit the opposite ends 48 and 50 of the skin contact layer 16 to overlap one another as shown in FIG. 7 when the bandage is applied to a body part such as a finger or the toe 96, in order to securely hold the bandage in place with the dome 28 located where it is needed to reduce shear and friction forces for prevention or treatment of skin breakdown.

Figure 8A:
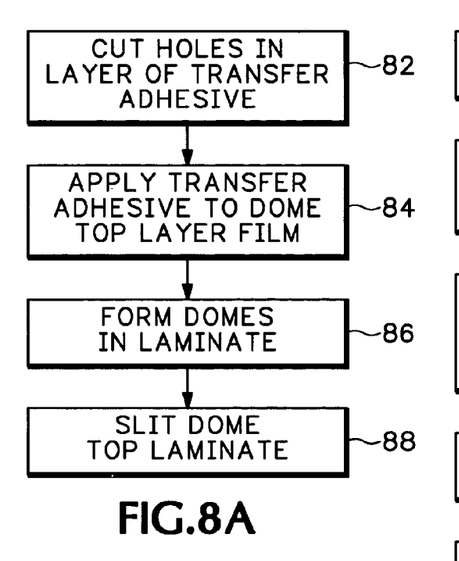
FIG. 8A is a flow diagram showing steps involved in manufacturing a dome top portion for the bandage shown in FIG. 1.

Referring to FIG. 8A, a friction reducing bandage such as the bandage 14 is preferably made using known production equipment for working with films of plastics or other webs of material, performing a novel combination of steps. As a first step, shown at 82 in FIG. 8, domes 28 are prepared by cutting openings corresponding to the size and shape of the dome 28 in a web of a transfer adhesive material to form the adhesive layer 44. The web of transfer adhesive material includes an easily released protective carrier sheet or liner of coated paper on at least one side of a layer of adhesive material. Once the openings have been cut in the layer of transfer adhesive material, the transfer adhesive is adhered to one side of a web of the 1 mil. polyethylene film material for the dome top layer 36, forming a laminate of the dome top layer 36, the layer 44 of adhesive, and the coated paper carrier, as indicated at 84. These first two steps may both be accomplished using a rotary converter apparatus such as, for example, the Crusader® Converter available from Delta Industries of Minneapolis, Minn., or an equivalent converter apparatus capable of unwinding, separating, guiding, combining, and rewinding multiple webs from individual spools while maintaining required alignments and registrations among the various webs.

Thereafter, as noted at 86, a dome 28 is formed in the dome top layer 28 within each opening through the layer 44 of adhesive, using heat and pressure to shape the polyethylene or other polymeric film. The domes 28 may be formed in sequentially produced arrays of several domes 28 produced simultaneously with each application of heat and pressure, using a machine such as is ordinarily used to form considerably thicker sheets of plastics materials to produce clam shell packaging. One such machine which has been found suitable for forming the very thin polyethylene film of the dome top layer 36 to produce an array of domes 28 and their skirts 42 for twenty-seven bandages 14 in each heating and pressing cycle is available from Preco Industries, Inc. of Lenexa, Kans., as its ConvertaForm™ forming system. This machine utilizes appropriate heated molds and dies in an automated air pressure forming system and can handle a forming area up to about 330×420 mm (13 inches by 16.5 inches) with each cycle. For the bandage 14, such domes are prepared using a tool to produce a dome initially having a height 33 of 0.250 in., including a flat top portion 30 with a diameter 31 of 0.900 in., interconnected with the side wall portion 32 by a radiused transition zone 92 whose radius 94 is preferably 0.125 in. but which may satisfactorily be within the range of 1.27–3.81 mm (0.050–0.150 in.). After formation of the domes 28, the polyethylene material typically retracts slightly so that the dome height 33 is ultimately about 4.76 mm (0.1875 in). The domes 28 are thus left free to move in any direction along the dome base layer 38, within the limitations established by the height 34 of the side wall portion 32, the extent of the transition zone 92, and the flexibility of the material of the dome top layer 36.

Instead of the top portion 30 being flat, it may also be formed to extend, for example, in the form of a portion of a spherical surface without adversely affecting the properties of the completed bandage 14.

After the domes 28 have been formed in the laminate of polyethylene dome top layer 36 and layer 44 of transfer adhesive material, the laminate is slit, as mentioned at 88, to form a continuous web of the laminate of the dome top layer 36 with domes 28 formed therein, the adhesive layer 44, and its cover sheet (not shown), bounded by the straight margins 58, and with the width 72 previously mentioned.

Figure 8B:
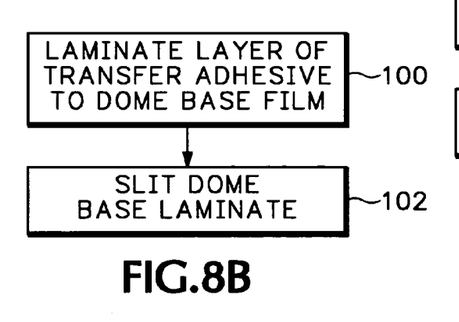
FIG. 8B is a flow diagram showing steps involved in assembling a dome base portion for the bandage shown in FIG. 1.

Referring next to FIG. 8B, using a rotary converter such as that previously mentioned, a layer of transfer adhesive to form adhesive layer 40 is laminated to a web of film material to be used as the dome base layer 38 as shown at 100. As shown at 102 the laminate of the dome base layer film and transfer adhesive is slit to form straight margins 52 separated by the required width 70.

Figure 9:
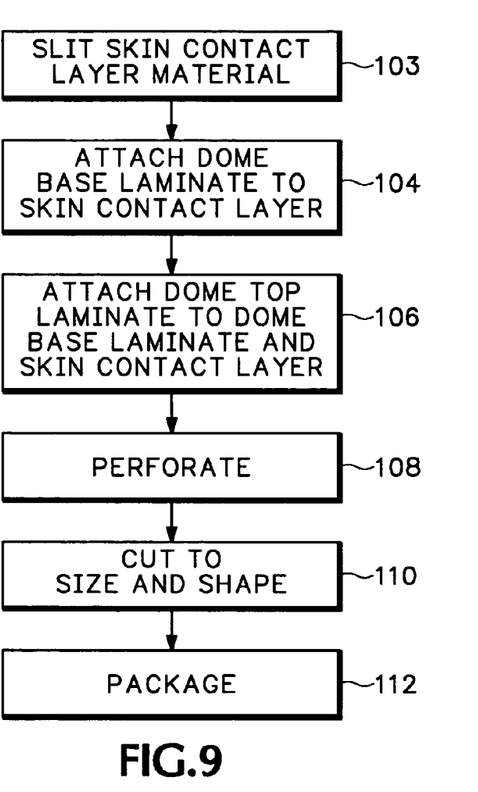
FIG. 9 is a flow diagram showing further steps according to the method of the present invention for manufacturing the bandage shown in FIG. 1.

As shown in FIG. 9, the bandages are assembled using a rotary converter such as the one described previously. First, a web of the required material for the skin contact layer 16 is slit to a width such as about 76 mm (3 in), wide enough to encompass the length 24 of the bandage 14, as indicated at 103.

Next, the dome base laminate of layers 36 and 40 formed as mentioned above at 102 is applied to the skin contact layer 16 by appropriately removing any carrier or liner from the layer 40 of transfer adhesive material, and the dome base layer 38 is placed on the skin contact layer 16 and fastened to it by the action of the adhesive layer 40, as shown at 104. The dome base layer 38 is aligned with a middle part of the skin contact layer web, so that its straight margins 52 face toward the sides of the slit web of skin contact layer material and are parallel with the length of that web of skin contact layer material.

Next, as noted at 106, the previously fabricated dome top laminate of domes 28, skirt portions 42, and adhesive layer 44 is attached to the dome base layer 38 and the skin contact layer 36 in proper alignment with the dome base layer 38, so that the straight margins 58 of the dome top layer 36 are located outside the straight margins 52 of the dome base layer and parallel with them. The skirt portion 42 of the dome top layer 36 is thus attached by the adhesive layer 44 both to the dome base layer 38 and to the carrier layer 16, where the margins 58 of the dome top layer 36 extend beyond the straight margins 52 of the dome base layer 38.

After the dome top layer 36 is attached to the dome base layer 38 and skin contact layer 16, each bandage 14 is appropriately perforated, 108, preferably by a sonic perforating machine associated with the converter. For example, a suitable sonic perforator is available from Branson Ultrasonic Corporation, of Danbury, Conn. The individual bandages 14 are then cut to finished size and shape, and the cut 22 is made in the liner 20, as shown at 110, preferably by die cutting, using the rotary converter. Alternatively, the liner 20 can be removed and replaced by a combination of liner portions of which one includes a margin folded back as a flap 23, shown in broken line in FIG. 1, before the individual bandages 14 are cut to finished size and shape.

The bandages 14 are then released from the surrounding areas of the laminated webs of skin contact layer 16, dome base layer 38, and dome top layer 36, and as noted at 112 the individual bandages are appropriately packaged.

Figure 10:
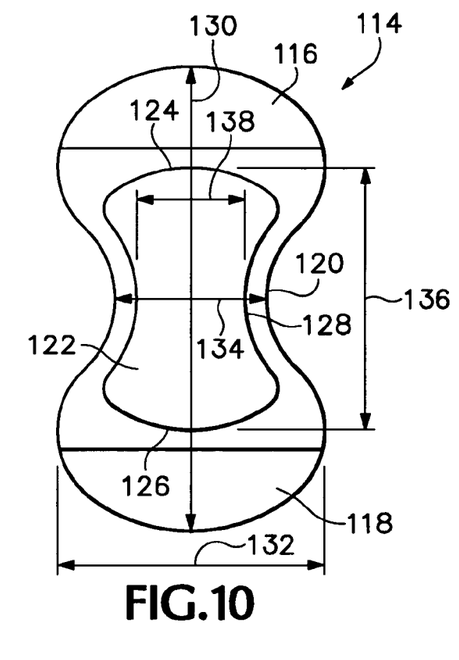
FIG. 10 is a top plan view of a bandage which is an alternative embodiment of the invention.

Referring next to FIG. 10, a bandage 114 is of similar construction to the bandage 14, but is of a different shape, resembling a figure-of-eight having a pair of enlarged end portions 116 and 118 and a narrow waist portion 120. A dome 122 of the bandage 114 also has a pair of convexly arcuate end portions 124 and 126 that are interconnected by a narrower waist portion 128. Such a bandage 114 is intended principally for use to protect convex portions of one's anatomy, such as elbows, heels, fingers, and toes, and can be made in a range of sizes, with a preferred overall length 130 of 57 mm (2.25 in.) and an overall width 132 of 31.75 mm (1.25 in.), with a waist width 134 of 22.23 mm (0.875 in.). The overall length 130 and overall width 132 could be varied within a range of at least ±½ in.

The dome 122 is significantly shorter than the overall length 130 to provide ample adhesive-carrying area in the end portions 124 and 126 of the skin contact layer, to attach the bandage securely to a person's skin. The dome 122 thus has a preferred overall length 136 of about 35 mm (1.375 in.) and an overall width 138 of about 12.7 mm (0.5 in.), although both of these dimensions could be varied within a range of at least ±6.3 mm (0.25 in.). The height of such a dome could be within the range of 4–6 mm. (0.18–0.25 in.).

Figure 11:
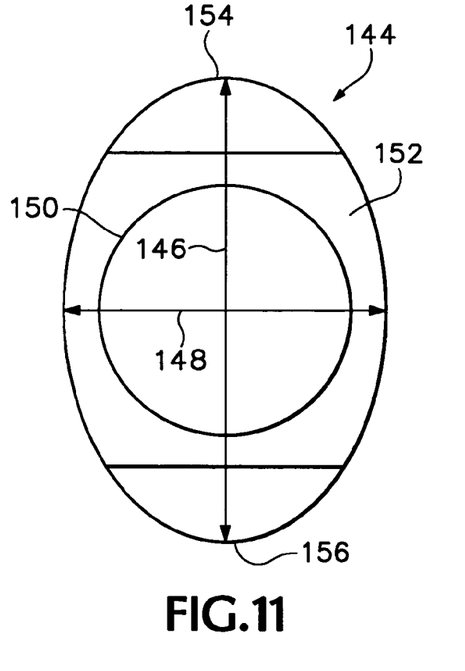
FIG. 11 is a top plan view of a bandage which is another alternative embodiment of the present invention.

Referring next to FIG. 11, a bandage 144 has an oval shape and may be elliptical, for example, with an overall length 146 of 108 mm (4.25 in.) and an overall width 148 of 76.2 mm (3 in.), both of which could be varied by as much as ±19 mm (±0.75 in.). A centrally located circular dome 150, whose diameter is preferably about 57.2 mm (2.25 in.), or could be varied within ±9.5 mm (±⅜ in.) of that size, is provided to correspond with the length 146 and width 148 of the bandage 144. The bandage 144 has an amply wide skirt portion 152 surrounding the dome 150 and also has some extension of a suitably flexible and elastic skin contact layer at each of the ends 154 and 156. The larger size of the bandage 144 by comparison with the previously described bandages 14 and 114 makes the bandage 144 more appropriate for use in prevention and treatment of pressure ulcers. The bandage 144 is preferably manufactured of film materials and adhesives such as those described above, or of variations of those materials having a different moisture vapor transference rate. Such a bandage could be used in locations such as a person's sacrum (lower back), greater trochanter (hip), gluteus maximus (buttocks), heels, or elbows.

The bandage could also be produced with the dome and skin contact layer in other shapes to be used in other particular applications, without departing from the invention.

Figure 12:
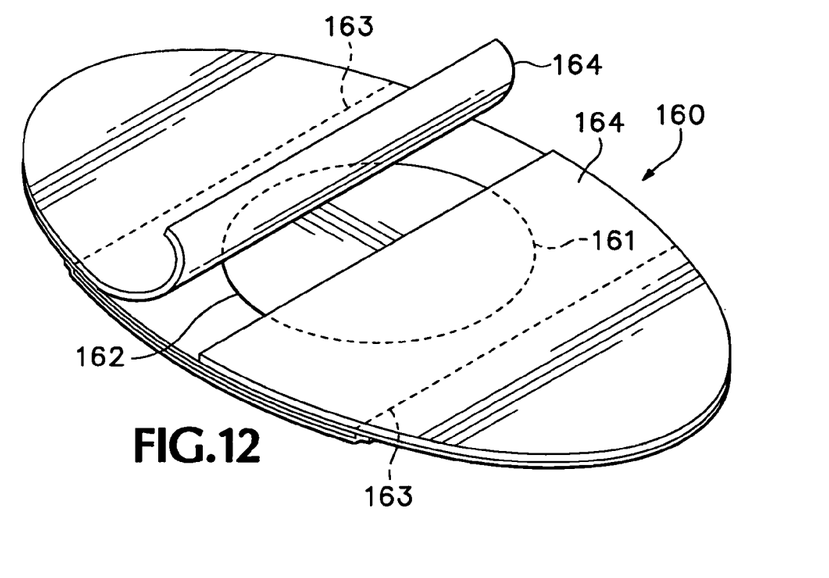
FIG. 12 is a partially cutaway isometric view taken from the bottom side of a bandage which is another alternative embodiment of the present invention.

The size of the bandage 14 could also be varied, keeping the same proportions to provide a bandage 14 whose size is, for example, 20 percent larger or 40 percent larger than previously mentioned, in order to protect an area of a patient's skin with an appropriately large bandage.

Where skin that is already blistered or abraded is to be treated to enhance healing of such skin, a bandage 160 shown in FIG. 12, may be utilized. Although the bandage 160 may generally be similar to the bandage 14, in an area 161 corresponding generally in size and shape to the dome, and optionally including the area 163 of the skirt portion of the dome top layer and the area of the dome base layer, the adhesive carrying lower or second side of the skin contact layer may be left without a layer of adhesive, or may be provided with a layer 162 of an adhesive translucent, flexible hydrocolloid material. Such a hydrocolloid material, once the liner 164 has been removed from the bandage, is placed in contact with the patient's sore or abraded skin or other wound and can absorb wound exudate, promote a moist wound-healing environment, and provide cushioning. Such a hydrocolloid material is available, for example, from Avery Dennison Medical, of Mentor, Ohio, as its MED 2190H, an 18 mil hydrocolloid, low peel force, transfer adhesive tape. Similar material may also be used in various thicknesses in a range of 10 to 50 mils for various applications.

A device embodying the present invention could also be applied to a surface of a device or an article of clothing, rather than to the user's skin. For example, a layer of a suitable material corresponding to the skin-contact layer 16 could be attached by sewing, or other bonding technique, i.e., heat or ultrasound, to the inside of a user's apparel, i.e., underwear, sock or shoe. It could also be attached to the inside of a shoulder pad, elbow pad or backpack strap, etc., for use in athletic or recreational activities.

In order to deal with other possible circumstances, friction reducing devices embodying the present invention could be incorporated into many articles during original manufacture of such articles, such as hospital mattress covers, wheelchair cushions, bicycle seats, shoe inserts, removable heel counters for shoes, other locations in the interior of shoes, socks, undergarments, straps for undergarments, and backpacks.

Figure 13:
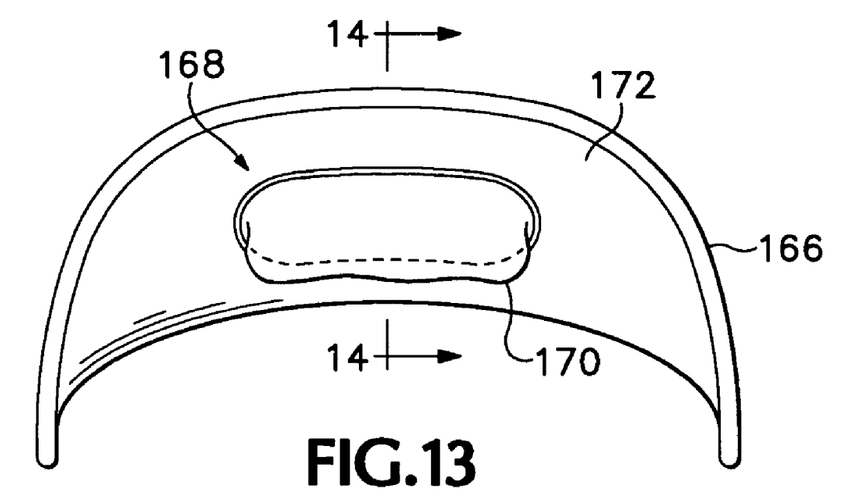
FIG. 13 is a perspective view from the upper front side of a heel counter insert for use in a sports shoe, including a friction-reducing device according to the present invention.
Figure 14:
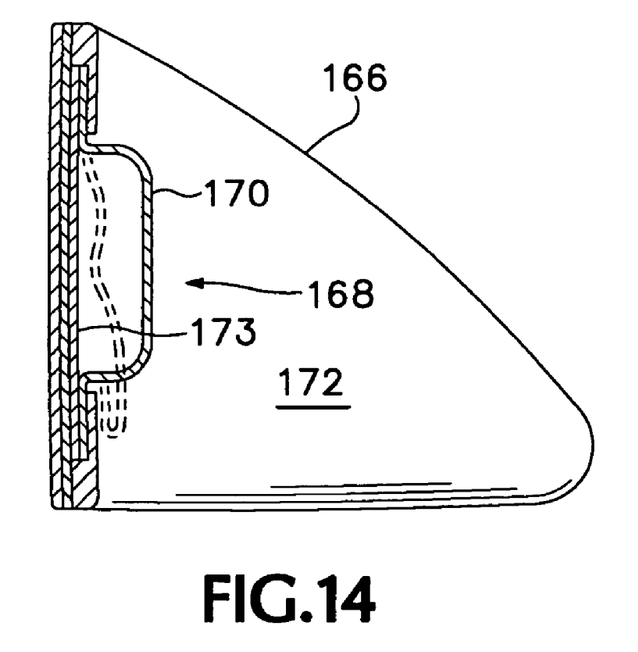
FIG. 14 is a sectional view of the heel counter insert shown in FIG. 13, taken along line 14—14 of FIG. 13.

For example, FIGS. 13 and 14 show a removable heel counter 166 for a sports shoe, incorporating a friction reducing device 168 according to the present invention in which a dome 170 is exposed on an inward-facing surface 172 of the removable heel counter 166. The friction reducing device 168 may also include a dome base layer 173, between the dome 170 and a dome supporting layer 174. The dome base layer 173 would be attached to the dome supporting layer 174 and be of material over which the dome 170 can glide freely. The friction reducing device 168 thus incorporates structures capable of performing the function of a friction reducing bandage 14, as described above, in the supporting structure of a heel counter 166, which may be a removable shoe accessory or a permanent part of a shoe.

The dome supporting layer 174 of such a friction reducing device 168 corresponds to the skin contact layer 16 of the bandage shown in FIGS. 1–5 and may be of a thicker material, and may be thermally laminated into the structure of the heel counter 166 itself. If a dome base layer 173 is not included, the dome supporting layer 174 should be of material that would not interfere with the gliding motion of the dome top layer 170. Instead of the thin polyurethane film material of the skin contact layer 16, the supporting layer 174 is preferably of a thicker film or may be of a durable, sturdy textile fabric, such as a woven cloth or knitted textile material, or of a different plastic such as a film or sheet of polyamide or polyester compatible with the adjacent material of the rest of the heel counter 166, since greater durability than for a bandage is preferred.

Figure 15:
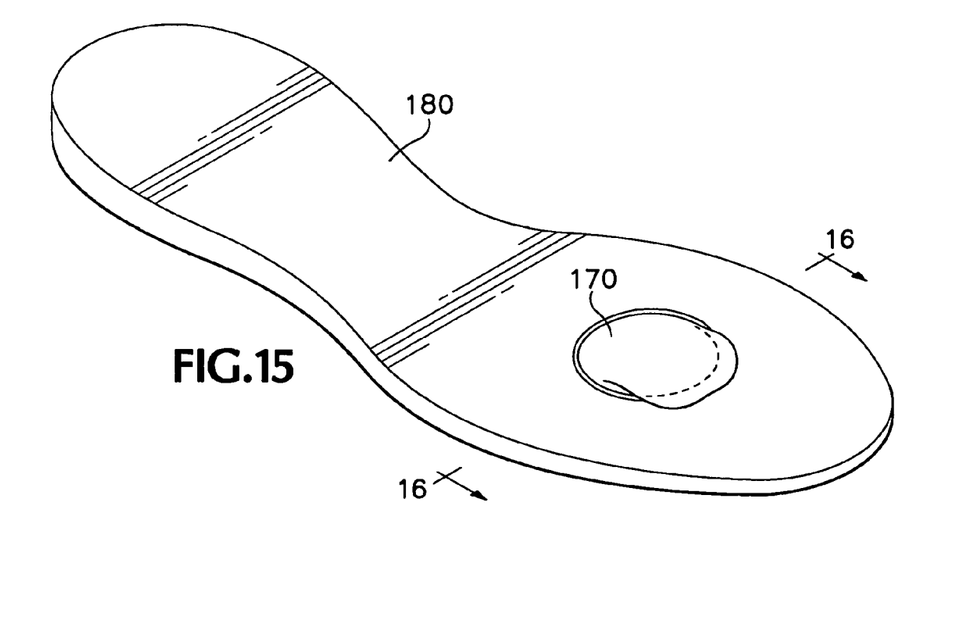
FIG. 15 is a perspective view of an insole, including a friction-reducing device according to the present invention.
Figure 16:
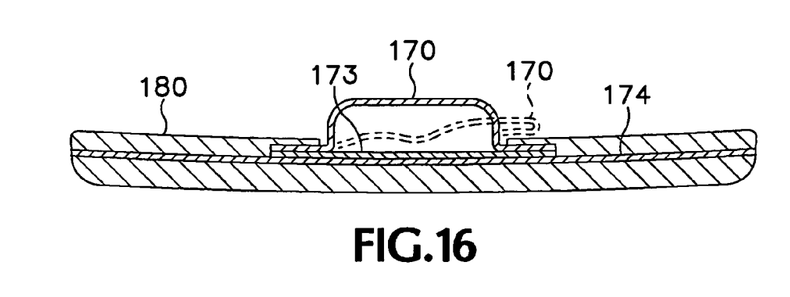
FIG. 16 is a sectional view of the insole shown in FIG. 15, taken along line 16—16 of FIG. 15.

In a different article such as a replaceable accessory insole 180, shown in FIGS. 15 and 16, the supporting layer 174 could also be of a plastic material such as polyurethane, suitable to be molded into, or inserted between other layers of the structure of the article concerned, to provide a secure incorporation of a friction reducing device 182 according to the present invention. The friction reducing device 182 also includes a dome 170 which is carried by a supporting layer 174 and exposed to be contacted by the user's foot to function in the same way as the dome 28.

The friction reducing domes 170 can be manufactured in generally the same fashion as that described above with respect to the bandage 14, with modifications as necessary to the supporting layer 174 depending on the article in which the friction reducing device is being incorporated.

Figure 17:
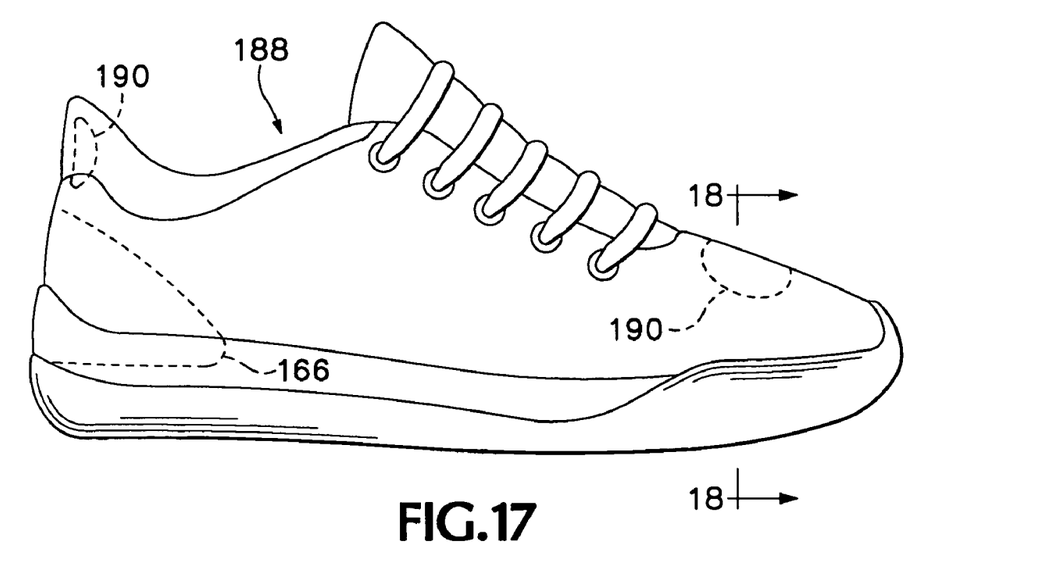
FIG. 17 is a side elevational view of a sports shoe incorporating friction-reducing devices according to the present invention.
Figure 18:
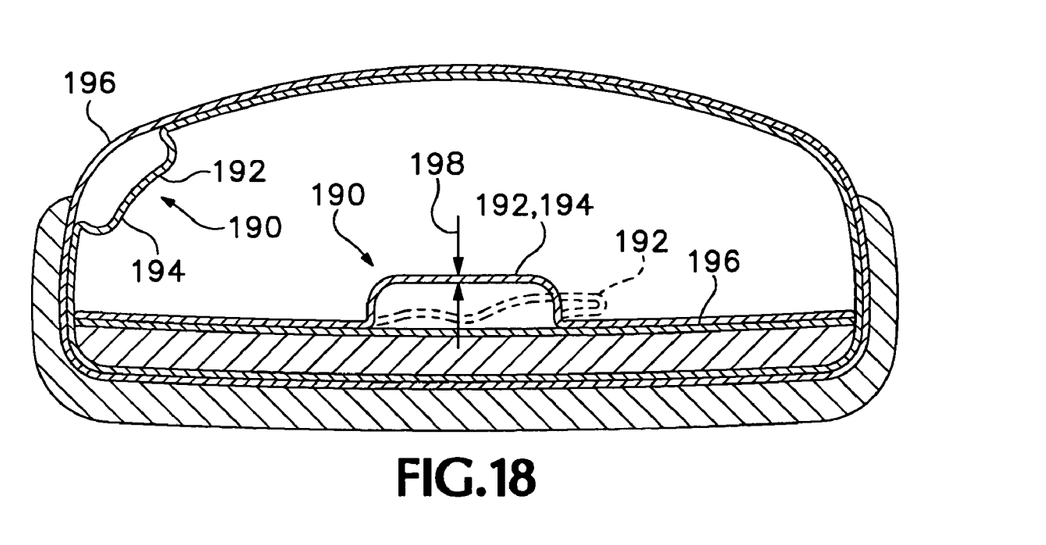
FIG. 18 is a sectional view taken along line 18—18 of FIG. 17.

As shown in FIGS. 17 and 18, as an example of including a similar friction-reducing device in an article of sports equipment or other application such as those mentioned above, a shoe 188 may incorporate friction-reducing devices 190 each including an integral dome 192 that functions in generally the same way as the dome 28. The friction reducing device 190 may be located in a permanently included heel counter portion of the shoe, in a heel collar, in the permanent insole, or at another critical place in the upper of such a shoe 188.

In order to ensure reasonably long durability of the friction-reducing device 190 incorporated in an article of clothing or sports or other equipment such as the shoe 188, a dome top layer 194 and dome base layer 196 may be made of a flexible material of greater strength than the 25 microns-thick polyethylene film used as the dome top layer 36 of the bandage 14 described above. For example, a polyethylene film material having a greater thickness 198, in the range of 25 microns to 1.525 mm (1–60 mils) would be satisfactory. Instead of polyethylene, another polymeric material such as a polyester film or a soft and closely woven or knitted textile fabric might be used, although it might require the use of a small amount of a lubricant between the dome top layer 194 and the dome base layer 196. More preferably, the top layer 194 and bottom layer 196 are appropriately formed and interconnected portions of the textile fabric, plastic-impregnated fabric, or plastic film of which the shoe 188 or other article is constructed, thin enough to be easily flexible, and lubricated as necessary to be able to slip readily along each other. Such formation and interconnection of the layers of material to form the domes 192 is performed as part of the process of assembling the article including the domes 192.

The terms and expressions that have been employed in the foregoing specification are used therein as terms of description and not of limitation, and there is no intention, in the use of such terms and expressions, of excluding equivalents of the features shown and described or portions thereof, it being recognized that the scope of the invention is defined and limited only by the claims that follow.

The invention claimed is:

1. A protective bandage, comprising:
   (a) a skin contact layer of flexible film having opposite first and second sides;
   (b) a collapsible hollow dome of flexible film attached to and extending over a portion of said first side of said skin contact layer, said hollow dome having a height at least partially defined by a side wall of flexible film, and a top portion, said skin contact layer extending beneath all of said dome and the top portion being freely movable along said first side of said skin contact layer through a distance related to said height; and
   (c) said second side being adhesively attachable to a surface intended to be protected.

2. The bandage of claim 1, further including a layer of an adhesive material carried on at least a portion of said second side of said skin contact layer.

3. The bandage of claim 2, wherein said layer of an adhesive material is coextensive with said second side of said skin contact layer.

4. The bandage of claim 2, wherein said layer of an adhesive material is absent from an area of said second side of said skin contact layer opposite and aligned with said dome.

5. The bandage of claim 1 including an array of perforations extending through said skin contact layer outside said portion thereof over which said dome extends.

6. The bandage of claim 5 wherein said perforations have a largest dimension in the range of 0.25 mm to 1.27 mm.

7. The bandage of claim 6 wherein said perforations are spaced apart from one another within said array by a distance in the range of 0.03 in to 0.09 in.

8. The bandage of claim 1 wherein said hollow dome includes a dome top layer of said flexible film, said dome top layer including a skirt portion surrounding and extending away from said dome and adhesively attached to said skin contact layer.

9. The bandage of claim 8 including a layer of an adhesive material conforming to said skirt portion and fastening said skirt portion to said skin contact layer.

10. The bandage of claim 8 wherein said dome top layer includes a said flexible side wall as a portion extending from said skirt portion to said top portion.

11. The bandage of claim 10 wherein said top portion of said dome is flat and extends parallel with said skirt portion of said dome top layer.

12. The bandage of claim 11, including an arcuate transition portion interconnecting said sidewall with said top portion of said dome.

13. The bandage of claim 8 wherein said skin contact layer is larger than said dome top layer.

14. The bandage of claim 13 wherein said skin contact layer is elongate and extends beyond said dome top layer in both of a pair of opposite directions.

15. The bandage of claim 8, wherein said skirt portion has a margin including a straight portion, said skin contact layer extends away from said dome top layer beyond said straight portion, and said bandage includes an array of perforations that extend through said skin contact layer, but wherein said bandage is free of perforations throughout an area extending a predetermined distance from said straight portion of said margin.

16. The bandage of claim 15 wherein some of said perforations extend through said skirt portion.

17. The bandage of claim 1 wherein said height of said dome is at least 4 mm.

18. The bandage of claim 1 wherein said bandage has a thickness not greater than 0.153 mm.

19. The bandage of claim 1 wherein said hollow dome includes a dome top layer of said flexible film and said dome top layer is thinner than said skin contact layer.

20. The bandage of claim 1 wherein said hollow dome includes a dome top layer of said flexible film and said skin contact layer is of a material which is more elastic than said dome top layer.

21. The bandage of claim 1 wherein said hollow dome includes a dome top layer of said flexible film and said flexible film of said dome top layer is sufficiently pervious to gas that said dome is substantially collapsed when said bandage is in use.

22. The bandage of claim 1 wherein said dome is circular.

23. The bandage of claim 22 wherein said skin contact layer is oval.

24. The bandage of claim 1 including a lubricant between said dome top portion and skin contact layer.

25. The bandage of claim 1 including a layer of a hydrocolloid material covering a portion of said second side of said skin contact layer.

26. A method of making a bandage, comprising:
   (a) shaping a flexible film to form a flexible dome including a flexible side wall and a top portion, leaving said dome surrounded by a generally planar skirt of said flexible film extending radially outward from said dome; and
   (b) thereafter attaching said skirt adhesively to a generally planar skin contact layer of a flexible film that extends at least beneath all of said dome, so that said dome is collapsible and said top portion is movable along said skin contact layer.

27. The method of claim 26 wherein said step of attaching said skirt to said skin contact layer includes forming an opening corresponding to said dome in a layer of transfer adhesive, and thereafter attaching said transfer adhesive layer to said skirt and to said skin contact layer.

28. The method of claim 26 including the further step of adhesively attaching a generally planar dome base layer of flexible film to said skin contact layer in position to extend at least beneath all of said dome, prior to said step of attaching said skirt to said skin contact layer, and wherein said step of attaching said skirt to said skin contact layer includes attaching a portion of said skirt adhesively to said dome base layer.

29. The method of claim 28 wherein said step of attaching said dome base layer adhesively to said skin contact layer includes attaching a layer of transfer adhesive to said dome base layer and to a first side of said skin contact layer.

30. The method of claim 26 including the further step of forming an array of small, closely spaced perforations through said bandage.

31. In combination with an article for use by a person, a friction reducing device, comprising:
   (a) a supporting layer of flexible material having opposite first and second sides;
   (b) a hollow dome of flexible material attached to and extending over a portion of said first side of said supporting layer, said hollow dome having a height and a top portion, the top portion being freely movable along said first side of said supporting layer through a distance related to said height; and (c) said second side being attached to a portion of said article of clothing so that said hollow dome is exposed toward a surface intended to be protected.

32. The combination of claim 31 wherein the article of clothing is a shoe.

33. The combination of claim 31 wherein the flexible material of the dome includes a polymeric film.

34. The combination of claim 31 wherein the flexible material of the dome includes a textile fabric.

35. A removable accessory for an article of clothing, including a friction reducing device comprising:
   (a) a supporting layer of flexible material having opposite first and second sides;
   (b) a hollow dome of flexible material attached to and extending over a portion of said first side of said supporting layer, said hollow dome having a height and a top portion, the top portion being freely movable along said first side of said supporting layer through a distance related to said height; and
   (c) said second side being attached to a portion of said removable accessory so that said hollow dome is exposed to a surface intended to be protected when said accessory is in use.

36. The combination of claim 35 wherein said removable accessory includes a heel counter for a shoe.

37. The combination of claim 35 wherein said removable accessory includes an insole for a shoe.

38. The combination of claim 35 wherein said flexible material of said hollow dome includes a polymeric film.

39. The combination of claim 35 wherein said flexible material of said hollow dome includes a textile fabric.

40. A method of making a bandage, comprising:
   (a) shaping a flexible film to form a flexible dome including a flexible side wall and a top portion, leaving said dome surrounded by a generally planar skirt of said flexible film extending radially outward from said dome; and
   (b) thereafter attaching said skirt adhesively to a skin contact layer of a flexible film extending at least beneath all of said dome, leaving said side wall between said skin contact layer and said top portion of said dome free to flex, thereby leaving said dome collapsible and said top portion movable along said skin contact layer to an extent limited by said side wall.

41. The method of claim 40 including the further step of adhesively attaching a dome base layer of flexible film to said skin contact layer prior to said step of attaching said skirt to said skin contact layer, and wherein said step of attaching said skirt to said skin contact layer includes placing said dome over said dome base layer and attaching a portion of said skirt adhesively to said dome base layer, leaving said side wall free to flex and thereby leaving said top portion free to move along said dome base layer.

42. The method of claim 40 including perforating said flexible dome.

43. The method of claim 26 including perforating said flexible dome.

44. The bandage of claim 1 wherein said dome is substantially collapsed and some of said top portion is in contact against said skin contact layer.

\* \* \* \* \*